United States Patent [19]

Lemole

[11] Patent Number: 5,232,691
[45] Date of Patent: * Aug. 3, 1993

[54] PROTECTIVE GEL COMPOSITION

[76] Inventor: Gerald M. Lemole, 404 Tomlinson Rd., Huntingdon Valley, Pa. 19006

[*] Notice: The portion of the term of this patent subsequent to May 28, 2008 has been disclaimed.

[21] Appl. No.: 703,973

[22] Filed: May 22, 1991

Related U.S. Application Data

[63] Continuation-in-part of Ser. No. 343,417, Apr. 26, 1989, Pat. No. 5,019,604.

[51] Int. Cl.$^5$ .................. A61K 7/40; A61K 9/06; A61K 31/74
[52] U.S. Cl. .................. 424/78.02; 424/78.03; 424/78.07; 424/78.08; 424/400; 424/443; 424/641; 424/642; 424/195.1; 514/772.3; 514/783; 514/787; 514/944; 514/969; 514/975; 523/105; 523/122
[58] Field of Search .................. 523/105; 424/78, 81, 424/641, 642, 400; 514/969

[56] References Cited

U.S. PATENT DOCUMENTS

| | | | |
|---|---|---|---|
| 3,100,180 | 8/1963 | Smith et al. | 167/91 |
| 3,541,205 | 11/1970 | Hardigan et al. | 424/60 |
| 3,824,218 | 7/1974 | McKenna | 424/78 |
| 3,872,040 | 3/1975 | Mollohan et al. | 260/21 |
| 4,035,506 | 7/1977 | Lucas et al. | 514/547 |
| 4,478,853 | 10/1984 | Chaussee | 424/70 |
| 5,019,604 | 5/1991 | Lemole | 424/78 |

FOREIGN PATENT DOCUMENTS 105657 4/1984 European Pat. Off. .
255902 2/1988 European Pat. Off. .

OTHER PUBLICATIONS

Oz, Mc., et al., "Prevention of Radioactive Indicator And Viral Particle Transmission With An Ointment Barrier", *Infection Control and Hospital Epidemiology*, vol. 12, No. 2, pp. 93–95 (Feb., 1991).
*Derma Shield* TM Fact Sheet (dated Apr., 1991).
*Dermo-Film Under-Glove* TM Advertisement (published prior to May 22, 1991).
*Dermo-Film Under Glove* TM photocopy of product label (Distributed prior to May 22, 1991).

*Primary Examiner*—Thurman K. Page
*Assistant Examiner*—James M. Spear

[57] ABSTRACT

A protective gel composition for coating skin surfaces, prior to covering skin with standard surgical gloves of other covers. The protective gel composition comprises controlled proportions in mixture by weight of the following components: (a) a water-insoluble base, (b) a water-repellent agent, (c) a water-insoluble surfactant and (d) a binder which binds together the components of the composition.

22 Claims, No Drawings.

PROTECTIVE GEL COMPOSITION

CROSS-REFERENCE INFORMATION

This is a continuation-in-part application of application Ser. No. 07/343,417, filed Apr. 26, 1989, now U.S. Pat. No. 5,019,604.

FIELD OF THE INVENTION

The present invention relates to protective gel compositions for coating the skin and/or mucosa; and more particularly, to an improved protective gel having water-repellent qualities which are especially useful, for example, as a skin shield on the hands of medical personnel wearing surgical gloves.

BACKGROUND OF THE INVENTION

Medical personnel attending to a surgical procedure are at great risk to come into contact with patient blood. A serious danger exists with such exposure in the event the blood is infectious and comes into immediate contact with the skin or mucosa of the surgical personnel.

Surgical gloves and other body covering, traditionally worn to maintain sterile environment in operating rooms, can provide a certain barrier to an infectious exposure to blood from the surgical patient having, for example, hepatitis or Acquired Immune Deficiency Syndrome (AIDS). Surgical gloves, however, may have microscopic holes or openings therein which either occur during manufacture or which form while being worn.

Microscopic holes which occur during glove manufacture are extremely difficult to detect. On the other hand, those which occur while being worn will not generally be known, if at all, until after harmful exposure has been effected. Inasmuch as the hands of the surgical personnel may possess abrasions or cuts that provide a source of entry for the infectious disease, it is essential that their hands be afforded greater protection than that provided by standard surgical gloves.

In a typical operating room scenario, the undetected holes that occur in surgical gloves are only recognized by evidences of blood upon the hands of the surgical personnel after the surgical procedure is completed and the gloves have been removed. Indeed, health professionals are much more likely to come into contact with contaminated blood in this manner than by a needle stick, since personnel often have minute cuts, abrasions, and skin rashes which can be a portal of entry. In such working environments, therefore, it is imperative that a protective coating be applied to the hand surfaces beneath standard surgical gloves as a shield against skin contact from blood and blood products that may penetrate the gloves and otherwise cause infection of personnel. Most desirable in a gel form, such a protective coating should be sterilizable, non-toxic, maintain its physical properties at body temperature, be hydrophylic and water insoluble. It should further be non-reactive with the latex rubber of conventional surgical gloves, act as a lubricant during hand insertion into the gloves, remain on the site of application for several hours during any procedure, and be readily removed thereafter.

While numerous protective gel compositions have been developed for topical application to the skin, such compositions have generally been used for the temporary treatment of surface wounds, providing a water-soluble coating impermeable to air-ridden germs and bacteria. While these water-soluble compositions have provided satisfactory protective coatings that prevent germs and bacteria in the air from reaching the skin surface, they have not provided adequate protection from the biochemical hazards carried by blood and blood products to which the hands of surgical personnel are constantly exposed.

SUMMARY OF THE INVENTION

Accordingly, it is a general purpose and object of the present invention to provide an improved protective coating gel that effectively shields the skin and/or mucosa from exposure to infectious diseases.

Another object of the present invention is to provide a protective gel composition that coats the hands of surgical personnel beneath their gloves forming an impermeable barrier to biological hazards that may penetrate the gloves during surgical procedures.

Still another object of the present invention is to provide a sterilizable protective gel that is hypo-allergenic to the skin surface to which it is applied and non-reactive to the glove or other covering material worn over the skin.

An additional object of the present invention is to provide a protective gel that is sterilizable, hydrophylic, and water-insoluble, and further able to coat and fill in scratches, cuts abrasions, and other disorders that create a break in the skin continuity.

A further object of the present invention is to provide a protective gel composition that adheres well to the skin surface while also serving as a useful lubricant thereon for the placement of surgical gloves or other covers over the skin surface to be protected.

A still further object of the present invention is to provide a protective gel that is safe to apply to the skin, easy to remove after use, and economical to manufacture.

Briefly, these and other objects of the present invention are accomplished by a sterilized protective gel composition for coating skin surfaces, prior to covering skin with standard surgical gloves or other protective covers.

In one working example, the protective gel composition comprises controlled proportions in mixture by weight of the following components: (a) a water-insoluble base, (b) a water-repellent agent, (c) a water-insoluble surfactant and (d) a binder which binds together the components of the composition. For the specific purposes of this invention, the components should, collectively, retain the following characteristics: water insolubility, hydrophylia, non-toxicity, sterilizability and inertia at normal body temperatures to skin and the protective cover which will be placed thereover. Medicaments (e.g., Anti-microbial and anti-viral agents), in addition to lubricants which do not contain functional groups which bind to, or interact with, the skin and/or mucosa, and crevice fillers may be further added to the protective gel composition.

In practice, the protective gel composition of the present invention is sterilized and applied to the skin just prior to placing the gloves or other protective covering thereover. This protective gel creates a water-repellent coating which prevents skin contact with body fluids, such as blood and blood products, that may penetrate the protective covering (e.g., gloves) and otherwise expose the skin to harmful microbial and viral infections. When the protective covering (e.g., gloves) is removed, the gel can be easily washed-off with an alcohol and liquid detergent solution.

Other objects, advantages and novel features of the present invention will become apparent from the following detailed description thereof.

DESCRIPTION OF THE PREFERRED EMBODIMENT

The present invention is a water-insoluble gel composition intended to be used as a protective intermediate coating for skin surfaces. While the present invention has many uses which will become apparent upon reading the detailed description, it is particularly useful as a means for protecting skin which is at risk of exposure to body fluids, such as blood and blood products, during a medical or surgical procedure. Since those skin surfaces at risk are generally covered with surgical gloves or the like, in order to provide skin protection and maintain a sterile environment, the protective coating of the present gel composition is applied directly upon the skin surface just prior to covering the skin with the glove. By doing so, the protective gel serves as an intermediate barrier against hazardous infections carried by the body fluids that may penetrate the glove cover. Conversely, the present gel also provides a barrier which prevents resident bacteria in the skin pores of the attendant medical personnel from coming into contact with the sterile environment through a microscopic hole in the glove.

In accordance with the present invention and the working examples set forth below, the protective gel composition of the present invention comprises the following components: (a) a water-insoluble base, (b) a water-repellent agent, (c) a water-insoluble surfactant and (d) a binder which binds together the components of the composition. Each component of the present composition is contained in a respective range of percentages, by weight, as detailed and explained below.

In addition to the aforementioned components, the present invention can also include additives which further enhance its utility. Examples of such additional components include, but are not limited to: lubricants which do not contain functional groups which bind to, or interact with, the skin, crevice fillers, and medicaments which specifically fortify the protective gel as a barrier against infectious carriers (e.g., anti-bacterial and anti-viral agents, such as nonoxynol-9 and povidone). The concentrations of such lubricants, fillers and medicaments in the present composition will vary depending upon the particular additive employed, but in all instances will be an amount effective for the intended purpose.

In regard to the specific ingredients contained in the present gel composition, the water-insoluble base comprises at least 50% by weight of the total composition. Preferably, the water-insoluble base is present in a concentration ranging from about 50% to about 90% by weight.

Any suitable water-insoluble base can be employed when practicing the present invention. The water-insoluble base is generally a cosmetically acceptable wax, which has the following characteristics: water insolubility, hydrophylia, non-toxicity and inertia at body temperatures. Examples of suitable water-insoluble bases having these characteristics include, but are not limited to: waxes of animals, minerals or plants, lanolin, paraffin, carnauba wax, beeswax, mineral wax, cocoa butter and petrolatum.

The presently preferred water-insoluble base is lanolin. The lanolin which is specifically preferred is substantially available in gel form. Such lanolin is generally produced from the grease of the wool of sheep. Additionally, synthetic substitutes for the lanolin having cosmetic characteristics similar thereto may be usefully employed as the water-insoluble base of the protective gel composition. For example, the combination of a polymerized hydrophylic acrylate and low-chain alcohol emollient provide a suitable substitute for lanolin in the present composition.

In the present composition, the water repellent agent provides the protective gel with sufficient characteristics of lubricity, sterilizability, inertia, non-toxicity and heat stability. In the present invention, the water-repellent agent comprises a minor portion of the total composition. Generally, its proportion is below about 10% by weight. Preferably, the amount of the water repellent agent in the composition ranges from between about 1.5% to about 6% by weight.

Any suitable water-repellent agent can be employed when practicing the present invention. Examples of such suitable agents include, but are not limited to, the group of liquid, organo-silicone polymers often referred to as "polysiloxanes". This well known class of compounds, also often referred to as "silicones", is commonly used in cosmetic preparations, offering properties of water repellency, slip, non-greasy emollience and low penetration of the skin. Such polysiloxane fluids are generally insoluble in water and are available in viscosities ranging from about 40 to about 100,000 centistokes at 25° C.

The presently preferred water-repellent agent is a dimethylpolysiloxane fluid. A suitable example of such a fluid is a commercially available product from the General Electric Co. known as "GE SF-96 Silicon Oil". Other water-repellent compounds from the group of organo-silicone polymers having the same or similar physical characteristics as that of the described liquid silicone may be used in combination with, or as a substitute for, the water-repellent agent in the present protective gel composition.

In the present composition, the surfactant serves as a spreading aid, dispersant and emollient. The surfactant generally employed is soluble in common alcohols and certain water/alcohol solutions, but generally is insoluble in water at 25° C.

In the present invention, the water-insoluble surfactant also comprises a minor portion of the total composition. Generally, its proportion is below about 10% by weight. Preferably, the amount of the water-insoluble surfactant in the composition ranges from about 1.5% to about 6% by weight.

Any suitable surfactant can be employed when practicing the present invention. Examples of such suitable surfactants include, but are not limited to: polypropylene glycols, and stearic acids.

The presently preferred surfactant is polypropylene glycol mono-oleate. The polypropylene glycol mono-oleate referred to herein and employed in the present protective gel composition is a commercially available surfactant in the chemical group of polypropylene glycol fatty acid esters. Moreover, Polypropylene glycol mono-oleate is a clear, light-colored liquid of relatively low viscosity, typically in the range of about 270 cps (Brookfield RVF) at 25° C. This surfactant exhibits high lubricity and good spreadability without being of a greasy or tacky nature. Other typical properties include an Acid Number of 1.3, a Saponification Number of 25.0, and a Specific Gravity of 0.99 at 25° C.

A specific propylene glycol mono-oleate which is especially useful when practicing the present invention is commercially available under the trade name "WIT-CONOL F26-46" and is manufactured by the Organics Division of Witco Chemical Corporation.

The present protective gel composition also comprises a binder. This binder binds the components of the gel composition together. Preferably, the binder also provides the gel composition with good adhesion qualities upon the skin surface to which it is applied.

In the present invention, the binder also comprises a minor portion of the total composition. Generally, its proportion is below about 10% by weight. Preferably, the amount of the binder in the composition ranges from about 1.5% to about 6% by weight.

Any suitable binder can be employed when practicing the present invention. One example of a suitable binder includes, but is not limited to, zinc oxide. The zinc oxide which is presently preferred when practicing this invention is a white, non-toxic powder which serves as a pigment, as well as an adherent which binds the ingredients together and which binds the composition to the skin.

As stated earlier, the present protective gel composition can, optionally, comprise components which enhance the gel's functional and protective nature. Examples of such optional components include, but are not limited to, agents which can fill crevices on the applied skin surface, agents which aid lubrication between the protective cover (e.g., gloves) and the skin, and medicaments.

A presently preferred agent which can be used for both, filling crevices on the applied skin and as a lubricant between the skin and the protective cover is a fluorine-containing polymer which contains substantially no functional groups which can bind or interact with the applied skin surface.

A specific fluorine-containing polymer which is especially useful when practicing the present invention is polytetrafluoroethylene (PTFE). If PTFE is employed as the optional, fluorine-containing polymer, it is presently preferred to have the PTFE in a powder (i.e., microspherical) form. One example of a specific PTFE suitable for use with this invention is commercially available under the trade name "TEFLON", manufactured by the DuPont Company.

If employed, the optional, fluorine-containing polymer is present in an amount ranging from about 1% to about 20% by weight; preferably, from about 2% to about 10% by weight, wherein said weight percentages are based on the total weight of the final composition.

If medicaments are employed they should be present in an amount effective for their intended use. A presently preferred medicament is nonoxynol-9 for its known effectiveness in inactivating HIV replication and the transmission of associated HIV infections. The effective range of the nonoxynol-9 in the present protective gel composition is between about 0.025% and about 1.0% by weight.

Another preferred medicament is povidone. In the case of povidone, the amount contained as a medicament in the protective gel composition of the present invention will generally range below about 10%; preferably from between about 5.0% and about 8.0% by weight.

Specific formulations of the protective gel composition are set forth below in respectively numbered examples, each on a weight percent basis.

EXAMPLE 1

| | |
|---|---|
| Lanolin | 88%–92% |
| Liquid Silicone-Dimethylpolysiloxane | 2%–5% |
| Zinc Oxide powder | 3%–5% |
| Polypropylene glycol mono-oleate | 3%–5% |
| Octoxynol | 0.5% |
| Methyl Paraben | 0.2% |
| Propyl Paraben | 0.1% |

The foregoing formulation of the present composition is prepared by warming the lanolin to just beyond its melting point (i.e., about 50° C.) and adding the zinc oxide powder thereto. As the temperature is maintained, and while thoroughly mixing, the polypropylene glycol mono-oleate and liquid silicone are added prior to allowing the composition to cool to ambient temperature.

After the aforementioned components are uniformly dispersed, the composition is cooled to ambient temperature to form a firm, creamy, yellow gel. The medicaments (i.e., octoxynol, methyl paraben and propyl paraben) are then added and uniformly dispersed throughout the gel composition prior to its sterilization. Sterilization can typically be performed by gamma irradiation.

EXAMPLE 2

| | |
|---|---|
| Lanolin | 83.8% |
| Liquid Silicone-Dimethylpolysiloxane | 3.0% |
| Polytetrafluoroethylene powder | 5.0% |
| Zinc Oxide powder | 7.7% |
| Nonoxynol-9 | 0.5% |

The foregoing formulation of the present composition is prepared by warming the lanolin to just beyond its melting point or to about 50° C. and adding the zinc oxide powder. As the temperature is maintained and while thoroughly mixing, the polytetrafluoroethylene powder is added until uniformly dispersed. To this mixture, the liquid silicone is added and further mixed together before allowing the composition to cool to ambient temperature at which a firm, creamy yellow gel is formed. The desired amount of medicament (nonoxynol-9 in the example above) may then be added to the gel composition prior to its sterilization, typically by gamma irradiation.

EXAMPLE 3

| | |
|---|---|
| Lanolin | 69.5% |
| Polypropylene glycol mono-oleate | 11.0% |
| Polytetrafluoroethylene powder | 6.0% |
| Zinc Oxide powder | 6.0% |
| Povidone | 7.5% |

The above formulation of the protective gel composition is prepared in like manner to that formulation of Example 2, with the povidone being added as a medicament in substantially greater amount than the nonoxynol-9 of the first formulation.

EXAMPLE 4

| Lanolin | 71.75% |
|---|---|
| Liquid Silicone-Dimethylpolysiloxane | 6.0% |
| Polypropylene glycol mono-oleate | 10.0% |
| Polytetrafluoroethylene powder | 6.0% |
| Zinc Oxide powder | 6.0% |
| Nonoxynol-9 | 0.25% |

This formulation is similarly prepared to that of the previously described examples, with the liquid silicone and polypropylene glycol mono-oleate being added together and mixed in respective proportions prior to addition of the nonoxynol-9 medicament.

EXAMPLE 5

| Lanolin | 80.0% |
|---|---|
| Liquid Silicone-Dimethylpolysiloxane | 5.0% |
| Polypropylene glycol mono-oleate | 10.0% |
| Polytetrafluoroethylene powder | 5.0% |
| Nonoxynol-9 | 0.05% |

The above formulation proved to have most effective results as a protective coating gel, being prepared similarly to that of Example 4 but without inclusion of the zinc oxide powder.

In accordance with one specific method of practicing the present invention, the protective gel composition is sterilized. The required sterilization can be effected by any suitable means known to those skilled in the art. Examples of such suitable means include, but are not limited to: gamma irradiation and gas sterilization.

After sterilization, the gel is applied to the surface of the skin to be protected. Typically, such topical application of the gel will occur upon the hands of surgical personnel in a sterile operating room environment immediately after the hands are scrubbed. Specifically, the scrubbed hands, coated with the protective gel, are inserted into standard surgical gloves. The presence of the present gel composition between the skin and gloves provides the surgical personnel with an additional protective physical and biochemical barrier during intra-operative use.

Beneath the covering of the surgical glove, the present gel composition provides a sterile, water-insoluble coating for the skin that does not dissolve or otherwise breakdown the conventional glove materials of latex rubber and the like. The coating is relatively thin but effective as a repellent barrier to water-based body fluids, such as blood and blood products, that may possibly penetrate the glove cover and carry bacterial or viral infections to the skin. Upon the skin surface and covered by the gloves, the coating of the present condition remains consistent and of gel-like viscosity, with the composition not liquifying or otherwise breaking down at the body temperature levels reached during use. At the end of the surgical procedure following the removal of the glove cover, the coating is easily wiped and cleaned from the skin by washing with alcohol and liquid detergent.

Therefore, some of the many advantages of the present invention should now be apparent. Generally, the described protective gel composition provides an improved coating that effectively shields the skin of medical personnel for several hours from harmful contact with body fluids and the consequent exposure to infectious diseases. More particularly, the present protective gel composition especially serves to coat the hands of surgical attendants beneath their glove thereby forming an impermeable barrier to microbial and viral hazards that may penetrate the gloves during surgical procedures.

The protective gel of the present invention is sterilizable for appropriate surgical use and is compatible with various medicaments (e.g., anti-bacterial and anti-viral agents) which fortify the protective coating. Additionally, the present protective gel is hypoallergenic to the skin surface to which it is applied and non-reactive to the surgical gloves or other coverings material worn over the skin.

The coating provided by the present gel composition adheres well to the skin surface while also providing a useful lubricant that facilitates the placement of the skin cover used over the surface being protected. The protective gel is safe and easy to apply, readily washable with alcohol and liquid detergent and economical to manufacture.

Obviously, any modifications and variations of the present invention are possible in light of the above teachings. For example, in addition to its employ as a skin coating to be applied beneath surgical gloves, the present protective gel composition can be effectively used as an ointment to be used in conjunction with condoms to protect the skin and mucosa from microbial and viral hazards. Furthermore, rather than being topically applied by the user upon the skin surface to be protected, the present gel composition may also be provided as an inner coating layer in the manufacture of the surgical glove or other skin covering and thus be intimately applied to the skin concurrently with the placement of the gloves or other coverings.

It is, therefore, to be understood that, within the scope of the appended claims, the invention may be practiced otherwise than as specifically described.

That which is claimed is:

1. A water-insoluble, protective, sterilizable gel composition for use as an intermediate layer between a skin surface and a protective cover, said water-insoluble gel composition comprising:
   (a) a water-insoluble base, wherein said water-insoluble base comprises at least one component selected from the group consisting of waxes of animals, minerals or plants, lanolin, parafin, carnauba wax, beeswax, mineral wax, cocoa butter, petrolatum and a synthetic substitute for lanolin having cosmetic characteristics similar thereto, and wherein at least 50% by weight of the total composition is comprised of said water-insoluble base;
   (b) a water-repellant agent, wherein said water-repellant agent comprises at least one liquid, organo-silicone polymer, and wherein up to about 10% by weight of the total composition is comprised of said water-repellant agent;
   (c) a water-insoluble surfactant, wherein said water-insoluble surfactant comprises at least one component selected from the group consisting of polypropylene glycols and stearic acids, and wherein up to about 10% by weight of the total composition is comprised of said water-insoluble surfactant; and
   (d) a binder means for binding together components (a), (b) and (c).

2. A protective, sterilizable gel composition as recited in claim 1, wherein said water-insoluble base comprises at least one composition selected from the group consisting of lanolin and a synthetic substitute for lanolin having cosmetic characteristics similar thereto.

3. A protective, sterilizable gel composition as recited in claim 2, wherein said synthetic substitute of lanolin comprises the combination of a polymerized, hydrophylic acrylate and low-chain alcohol emollient.

4. A protective, sterilizable gel composition as recited in claim 2, wherein said water-insoluble base comprises lanolin.

5. A protective, sterilizable gel composition as recited in claim 1, wherein said water-repellant agent comprises silicone oil.

6. A protective, sterilizable gel composition as recited in claim 1, wherein said water-insoluble surfactant comprises polypropylene glycol.

7. A protective, sterilizable gel composition as recited in claim 1, wherein said binder means comprises zinc oxide.

8. A protective, sterilizable gel composition as recited in claim 1, wherein said water-insoluble base comprises from about 50% to about 90% by weight of the total composition.

9. A protective, sterilizable gel composition as recited in claim 1, wherein said water-repellant agent is present in an amount ranging from about 1.5% to about 6% by weight of the total composition.

10. A protective, sterilizable gel composition as recited in claim 1, wherein said water-insoluble surfactant is present in an amount ranging from about 1.5% to about 6% by weight of the total composition.

11. A protective, sterilizable gel composition as recited in claim 1, wherein up to about 10% by weight of the total composition comprises said binder means.

12. A protective, sterilizable gel composition as recited in claim 11, wherein said binder means is present in an amount ranging from about 1.5% to about 6% by weight of the total composition.

13. A protective, sterilizable gel composition as recited in claim 1,
wherein said water-insoluble base is present in an amount ranging from about 50% to about 90% by weight,
wherein said water-repellant agent is present in an amount ranging from about 1.5% to about 6%,
wherein said water-insoluble surfactant is present in an amount ranging from about 1.5% to about 6% by weight, and
wherein said binder means is present in an amount ranging from about 1.5% to about 6% by weight, all of said aforementioned weight percentages being based upon the total weight of said gel composition.

14. A protective, sterilizable gel composition as recited in claim 13,
wherein said water-insoluble base comprises lanolin, wherein said water-repellant agent comprises silicone oil,
wherein said water-insoluble surfactant comprises polypropylene glycol and
wherein said binder means comprises zinc oxide.

15. A protective, sterilizable gel composition as recited in claim 1, wherein said composition further comprises at least one additional component selected from the group consisting of lubricants which do not contain functional groups which bind to, or interact with, the skin; crevice fillers; and, medicaments which specifically fortify said gel composition as a barrier against infectious carriers.

16. A protective, sterilizable gel composition as recited in claim 15, wherein said lubricant comprises a fluorine-containing polymer.

17. A protective, sterilizable gel composition as recited in claim 16, wherein said fluorine-containing polymer is present in an amount ranging from about 1% to about 20% by weight, said weight percentage being based upon the total weight of said gel composition.

18. A protective, sterilizable gel composition as recited in claim 17, wherein said fluorine-containing polymer comprises polytetrafluoroethylene.

19. A protective, sterilizable gel composition as recited in claim 15, wherein said gel composition comprises at least one medicament selected from the group consisting of nonoxynol-9, octoxynol, Povidone, methyl paraben and propyl paraben.

20. A method for protecting skin or mucosa comprising applying an intermediate coating of a sterilized, water-insoluble gel composition between the skin or mucosa to be protected and a protective cover, wherein said water-insoluble gel composition comprises:
(a) a water-insoluble base, wherein said water-soluble base comprises at least one component selected from the group consisting of waxes of animals, minerals or plants, lanolin, parafin, carnauba wax, beeswax, mineral wax, cocoa butter, petrolatum, and a synthetic substitute for lanolin having cosmetic characteristics similar thereto, and wherein at least 50% by weight of the total composition is comprised of said water-insoluble base;
(b) a water-repellant agent, wherein said water-repellant agent comprises at least one liquid, organo-silicone polymer, and wherein up to about 10% by weight of the total composition is comprised of said water-repellant agent;
(c) a water-insoluble surfactant, wherein said water-insoluble surfactant comprises at least one component selected from the group consisting of polypropylene glycols and stearic acids, and wherein up to about 10% by weight of the total composition is comprised of said water-insoluble surfactant; and
(d) a binder means for binding together components (a), (b) and (c).

21. A water-insoluble, protective, sterilizable gel composition for use as an intermediate layer between a skin surface and a protective cover, said water-insoluble gel composition consisting essentially of:
(a) a water-insoluble base, wherein said water-insoluble base comprises at least one component selected from the group consisting of waxes of animals, minerals or plants, lanolin, parafin, carnauba wax, beeswax, mineral wax, cocoa butter, petrolatum, and a synthetic substitute for lanolin having cosmetic characteristics similar thereto, and wherein at least 50% by weight of the total composition is comprised of said water-insoluble base;
(b) a water-repellant agent, wherein said water-repellant agent comprises at least one liquid, organo-silicone polymer, and wherein up to about 10% by weight of the total composition is comprised of said water-repellant agent;
(c) a water-insoluble surfactant, wherein said water-insoluble surfactant comprising at least one component selected from the group consisting of polypropylene glycols and stearic acids, and wherein up to about 10% by weight of the total composition is comprised of said water-insoluble surfactant; and (d) a binder means for binding together components (a), (b) and (c).

22. A method for protecting skin or mucosa comprising applying an intermediate coating of a sterilized, water-insoluble gel composition between the skin or mucosa to be protected and a protective cover, wherein said water-insoluble gel composition consists essentially of:

(a) a water-insoluble base, wherein said water-soluble base comprises at least one component selected from the group consisting of waxes of animals, minerals or plants, lanolin, parafin, carnauba wax, beeswax, mineral wax, cocoa butter, petrolatum, and a synthetic substitute for lanolin having cosmetic characteristics similar thereto, and wherein at least 50% by weight of the total composition is comprised of said water-insoluble base;

(b) a water-repellant agent, wherein said water-repellant agent comprises at least one liquid, organo-silicone polymer, and wherein up to about 10% by weight of the total composition is comprised of said water-repellant agent;

(c) a water-insoluble surfactant, wherein said water-insoluble surfactant comprising at least one component selected from the group consisting of polypropylene glycols and stearic acids, and wherein up to about 10% by weight of the total composition is comprised of said water-insoluble surfactant; and (d) a binder means for binding together components (a), (b) and (c).

* * * * *